United States Patent [19]
Gallo

[11] Patent Number: 4,983,552
[45] Date of Patent: Jan. 8, 1991

[54] METHOD FOR MAKING ORGANOSILAZANES

[75] Inventor: Anthony A. Gallo, Olean, N.Y.

[73] Assignee: The Dexter Corporation, Windsor Locks, Conn.

[21] Appl. No.: 237,515

[22] Filed: Aug. 26, 1988

Related U.S. Application Data

[60] Division of Ser. No. 936,473, Nov. 26, 1986, Pat. No.

[51] Int. Cl.$^5$ .................. C04B 35/56; C04B 35/58
[52] U.S. Cl. ........................... 501/92; 501/88; 501/96
[58] Field of Search .................... 501/90, 92

[56] References Cited

U.S. PATENT DOCUMENTS

| | | | |
|---|---|---|---|
| 3,036,019 | 5/1962 | Molotsky | 260/2 |
| 3,253,008 | 5/1966 | Fink | 260/448.2 |
| 3,408,379 | 10/1968 | McVannel | 260/448.2 |
| 3,579,557 | 5/1971 | Brooks | 260/448.2 N |
| 3,809,713 | 5/1974 | Boersma | 260/448.2 E |
| 3,853,567 | 12/1974 | Verbeek | 106/44 |
| 3,892,583 | 7/1975 | Winter | 106/55 |
| 4,115,427 | 9/1978 | Kotzsch | 260/448.2 E |
| 4,395,460 | 7/1983 | Gaul | 428/408 |
| 4,397,828 | 8/1983 | Seyferth | 423/344 |
| 4,482,669 | 11/1984 | Seyferth | 524/442 |
| 4,482,689 | 11/1984 | Haluska | 528/25 |

OTHER PUBLICATIONS

Syeferth et al., Polymer Preprints 25(2) 10 (1984).
Baney et al., Polymer Preprints 25(2) 2 (1984).
Ledbetter et al., J. Mat. Sci. Lett. 3 802 (1984).
Varshney, et al., Ceram. Eng. Sci. Proc. 3 555 (1982).
Coblenz et al., in *Emergent Process Methods for High Technology Ceramics*, ed. R. F. Davis et al., Plenum Publishing Corp. (1984).
Walker et al., Am. Ceram. Soc. Bull. 62(8) 916 (1984).
Rice, Am. Ceram. Soc. Bull. 62(8) 889 (1984).
Wynne et al., Ann. Rev. Mater. Sci. 14 297 (1984).
Penn et al., J. App. Polym. Sci. 27 3751 (1982).
Seyferth et al., Comm. Am. Ceram. Soc. 67 445 (1984).
Gaul, Chem. Abstracts 96: 163389e (1982).
Gaul, Chem. Abstracts 96: 143567h (1982).
Petrarch Chemical Co. Catalogue (1982) p. 215.
Bazant et al., "Organosilicon Compounds", vol. 1, Academic Press (NY 1965), p. 80.

*Primary Examiner*—William R. Dixon, Jr.
*Assistant Examiner*—Alan A. Wright
*Attorney, Agent, or Firm*—Fish & Richardson

[57] ABSTRACT

A method of preparing an organosilazane including reacting a first halosilane having the formula $RR^1SiX_2$, wherein X is F, Cl, Br, or I, and each R and $R^1$, independently, is X, H, or a lower alkyl group; a first primary amine compound having the formula $R^2NH_2$, wherein $R^2$ is H or a lower alkyl group; and a second primary amine compound having the formula $R^3NH_2$, wherein $R^3$ is H or a lower alkyl group, $R^3$ being different from $R^2$, to form the organosilazane.

14 Claims, No Drawings

METHOD FOR MAKING ORGANOSILAZANES

BACKGROUND OF THE INVENTION

This is a division of co-pending application Ser. No. 976,473, filed on Nov. 26, 1986, and a continuation-in-part of Gallo, U.S. Ser. No. 811,483, filed Dec. 20, 1985.

This invention relates to preparing organosilazanes.

Organosilazanes are organic compounds containing a backbone of silicon and nitrogen atoms, which can be polymerized to form polysilazanes. Polysilazanes are useful as ceramic-precursor polymers, forming upon pyrolysis, the ceramic materials silicon carbide and silicon nitride.

SUMMARY OF THE INVENTION

In general, the invention features a method for preparing an organosilazane involving reacting a first halosilane having the formula $RR^1SiX_2$, wherein X is F, Cl, Br, or I, and each R and $R^1$, independently, is X, H, or a lower (1 to 3 carbon atoms) alkyl group; a first primary amine compound having the formula $R^2NH_2$, wherein $R^2$ is H or a lower alkyl group; and a second primary amine compound having the formula $R^3NH_2$, wherein $R^3$ is H or a lower alkyl group, $R^3$ being different from $R^2$, to form the organosilazane.

In preferred embodiments, $R^2$, is H and $R^3$ is a lower alkyl group, most preferably $CH_3$; the first halosilane is a trihalosilane; and the first halosilane is reacted with the first primary amine compound to form a reaction product, which is then reacted with the second primary amine compound to form the organosilazane. Thus, the preferred method involves sequential addition of the primary amine compounds.

In other preferred embodiments, there is reacted with the first halosilane, first primary amine compound, and second primary amine compound a second halosilane different from the first halosilane and having the formula $R^4R^5R^6Si_x$, wherein X is F, Cl, Br, or I, and each $R^4$, $R^5$, $R^6$, independently, is X, H, or a lower alkyl group. Preferably, the composition of the two halosilanes and their mole ratio are selected so that the theoretical nitrogen to silicon ratio in the polymer formed from the organosilazane is 1.33. When the first halosilane is a trihalosilane (preferably $CH_3SiCl_3$ or $HSiCl_3$) and the second halosilane is a dihalosilane (preferably $CH_3SiHCl_2$ or $H_2SiCl_2$), the mole ratio of the first halosilane to the second halosilane is about 2:1. When the first halosilane is a dihalosilane (preferably $CH_3SiHCl_2$ or $H_2SiCl_2$) and the second halosilane is a tetrahalosilane (preferably $SiCl_4$), the mole ratio of the first halosilane to the second halosilane is also about 2:1.

The invention provides a simple and inexpensive method for preparing organosilazanes. The organosilazanes thus prepared are thermally stable at ambient temperatures and resist hydrolysis by atmospheric moisture for prolonged periods of time. In addition, they are readily polymerized under low temperature polymerization conditions (Preferably in an inert atmosphere at temperatures between about 200°–300° C.) to polysilazanes which are stable, fusible, and soluble in organic solvents, and which provide good yields of silicon nitride—silicon carbide upon pyrolysis. Preferably, pyrolysis is carried out in an inert atmosphere at temperatures between about 250°–1200° C. The pyrolysis products are thermally and oxidatively stable at high temperatures (>1000° C.) and can be used as protective coatings on fibers, e.g., carbon fibers.

Other features and advantages of the invention will be apparent from the following description of the preferred embodiments thereof and from the claims.

DESCRIPTION OF THE PREFERRED EMBODIMENTS

We now describe the synthesis and use of preferred organosilazanes of the invention.

In general, the synthesis involves reacting a halosilane with a primary amine compound, and then reacting the product of that reaction with a second primary amine compound different from the first. The synthesis can be represented as follows:

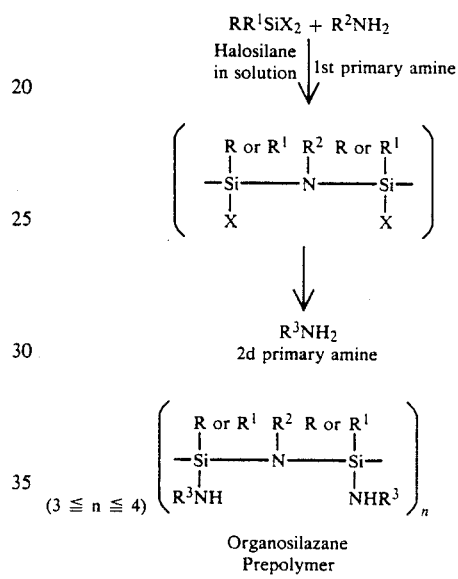

Since the final organosilazane contains R, $R^1$, $R^2$, and $R^3$, the molecular weight (and therefore the viscosity) of the organosilazane can be controlled by choosing the proper halosilane and primary amine starting materials. In addition, one can control the position of the R, $R^1$, $R^2$, and $R^3$ groups in the final organosilazane, e.g., if the two amines used are ammonia and methylamine, the methyl group will be bonded to the nitrogen atom of the organosilazane backbone if the methylamine is first reacted with the halosilane, and to the nitrogen atom not in the backbone if the ammonia is first reacted with the halosilane. The preferred reaction order is ammonia, followed by $CH_3NH_2$. Since the halogen atoms do not appear in the final organosilazane product, the choice of halogen is not crucial, but is governed primarily by the consideration of cost; chlorine is thus the preferred halogen.

The first step in the above-illustrated synthetic scheme is to dissolve the halosilane in a dry, inert, organic solvent such as toluene, tetrahydrofuran, or diethylether, such that the halosilane is present in the solvent at a concentration of 0.1 to 3.0 moles/liter. The solvent does not Participate in the reaction, and the solvent requirements are only that it be capable of dissolving at least 0.1 moles of halosilane/liter and that it not interfere with the reaction.

The next step is to react the solubilized halosilane with a primary amine $R^2NH_2$. In this step, the mole ratio of halosilane: amine is between 10:1 and 1:2; higher ratios generally yield material having a shorter N-Si spine, and thus lower viscosity and molecular weight. The amount of the first primary amine used should be low enough to ensure that the reaction product contains some reactive halogen atoms available for replacement by $R^3NH$ of the second primary amine. The reaction is carried at a temperature between about 20° and 60° C., for a period of 10 to 200 minutes. If the primary amine is a gas at the reaction temperature, it is bubbled through the solubilized halosilane; if it is a liquid, it can be added dropwise to the halosilane.

The next step is to react the product of the halosilane-amine reaction with the second primary amine. In this step, enough of the second primary amine is added so that all of the silicon-containing reactant is used. The reaction is carried out at a temperature of 20° to 60° C., for a period of 20 to 500 minutes. As in the case of the first primary amine, the second amine is bubbled through or added dropwise to the first reaction product. The organosilazane product is recovered, e.g., by filtering, and any remaining solvent is removed, e.g., by heating.

A particular organosilazane, of the formula

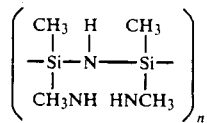

was synthesized from $CH_3SiCl_3$, and $CH_3NH_2$, as follows (these compounds are all commercially available).

$CH_3SiCl_3$ (4.5 kg) was added with stirring to approximately 22 gallons of dry toluene in a glass reactor fitted with an external stirrer, reflux condenser, drying tube filled with Drierite, and gas inlet tube. Anhydrous $NH_3$ was then bubbled through the gas inlet tube at a flow rate of approximately 3 liters/minute for 45 minutes. Dry $CH_3NH_2$ was then bubbled through the gas inlet tube until the Drierite in the drying tube turned blue, indicating excess amine. The solution was then filtered and the filtrate heated under vacuum to remove solvent. A yield of 25% based on $CH_3SiCl_3$ was obtained. The organosilazane is a viscous liquid with an ammoniacal odor and a molecular weight between 1,000–10,000.

The organosilazane can be polymerized to form a ceramic-precursor polysilazane by heating at a temperature between 200°–300° C. in an inert atmosphere. The polysilazane can then be pyrolyzed to form silicon nitride—silicon carbide. Alternatively, the polysilazane can be used to coat substrate fibers, e.g., carbon fibers, and then pyrolyzed to give a silicon nitride—silicon carbide coating on the substrate fibers. The coating increases the thermal and oxidative stability of the substrate fibers.

The polymerization of the particular organosilazane described formed from $CH_3SiCl_3$, $NH_3$, and $CH_2NH_3$, was carried out as follows. Organosilazane (1523 g) was added to a 2 liter three-neck round bottom flask equipped with a magnetic stir bar, reflux condenser, nitrogen inlet and outlet, and a thermometer. The flask was purged with nitrogen and maintained under a nitrogen atmosphere. The temperature was then increased slowly to 260° C. over a period of 7 hours to effect polymerization. At the end of this period, the product polysilazane was removed and cooled to solidify it. The average molecular weight of the polysilazane was 15,600, with a dispersity of 9.4. Elemental analysis results were in agreement with those calculated for a fully-crosslinked polymer: calculated for $CH_3Si[(NH)_x(NCH_3)_y]_{1.5}$ where $x=0.04$, $y=0.96$: C-30.9; H-9.5; N-25.5; Si-34.0; found: C-31.3; H-8.6; N-24.1; Si-30.2.

The above-described polysilazane was pyrolyzed to form silicon nitride—silicon carbide by placing a small sample (4.2 g) of the polymer in a ceramic crucible and loading the crucible in a furnace capable of sustaining 1200° C. for several hours. The crucible was then heated under a nitrogen atmosphere according to the following schedule.

| Temperature | Time |
|---|---|
| 275° C. –400° C. | 2 hours |
| 400° C – 760° C | 2 hours |
| 760° C – 1160° C | 1 hour |
| 1160° C | 1.5 hours |

The pyrolyzed residue in the crucible was then cooled to yield 2.4 g of silicon nitride—silicon carbide as a foamed black solid (57% yield).

Organosilazanes can also be prepared by reacting two different halosilanes with two primary amine compounds in a manner similar to that described above for one halosilane. The properties of the organosilazanes depend on the starting materials. Molecular weight increases with increasing molecular weight of starting materials. Generally, ease of polymerization increases with increasing halogen substitution of the halosilanes, and with an increasing ratio of highly halogen substituted to less highly substituted halosilanes, and decreases with the amount of alkyl amine used. Stability of polymerized preceramic product is increased by the use of some alkyl amine in organosilazane synthesis. Generally, where the halosilanes used are not highly halogen substituted, more ammonia than alkyl amine is used, for ease of polymerization; where the halosilanes used are more highly substituted, more alkyl amine than ammonia is used, for stability of product.

The halosilane combinations are preferably chosen to maximize the ceramic yield, i.e., the yield of silicon carbide and silicon nitride obtained upon pyrolysis of a polymer prepared from the organosilazane. It is believed that maximum yields are obtained when the theoretical nitrogen to silicon ratio in the polymer is about 1.33. This ratio is calculated by determining the polymer composition that would result if each halosilane individually reacted with the amine reactants.

For example, reacting $HSiCl_3$, $H_2SiCl_2$, $NH_3$, and $CH_3NH_2$ (where the mole ratio of $HSiCl_3$ to $H_2SiCl_2$ is 2:1) would yield the following: $2HSi(NZ)_{1.5}/H_2Si(NZ)$, where Z is H (from $NH_3$) or $CH_3$ (from $CH_3NH_2$). The ratio of the number of nitrogen atoms to the number of silicon atoms is 1.33. The ability to obtain this ratio depends on the functionalities of the halosilanes (i.e., whether the halosilanes are di-, tri-, or tetra-halosilanes), and the mole ratio of the respective halosilanes to each other. It has been found that combinations of a trihalosilane and dihalosilane at a ratio of 2:1 or a dihalosilane and tetrahalosilane at a ratio of 2:1 will yield the desired 1.33 theoretical ratio in the polymer.

Another way of maximizing the ceramic yield, while at the same time maximizing the proportion of silicon nitride compared to silicon carbide, is to maximize the degree of halogen substitution in the halosilane reactants. More silicon nitride is produced because there is less carbon available to form the carbide. Similarly, volatile by-products of the polymerization, which decrease the ceramic yield, tend to be hydrogen rather than hydrocarbon gas, e.g., methane, having higher molecular weights.

Preferred combinations of halosilanes include 2:1 mole ratios of $CH_3SiCl_3$ and $CH_3SiCl_2$; $CH_3SiHCl_2$ and $SiCl_4$; $HSiCl_3$ and $CH_3SiHCl_2$; $H_2SiCl_2$ and $SiCl_4$; and $HSiCl_3$ and $H_2SiCl_2$. The last two combinations are the most preferred.

Other combinations can also be used. Examples are $(CH_3)_2SiCl_2$ and $SiCl_4$; $CH_3SiCl_3$ and $CH_3SiHCl_2$; and $(CH_3)_3SiCl$ and $SiCl_4$. Neither mono- nor tetrasubstituted halosilanes should be used alone. Three or even four different halosilanes can be used together, and, as discussed above, two or more different primary amines can be used as well. The reactants can be added together or sequentially. The reaction conditions are generally the same as described above for one halosilane and two amines.

Other embodiments are within the following claims.

I claim:

1. A method of preparing silicon nitride-silicon carbide ceramic materials comprising the steps of
   forming an organosilazane by reacting
   (a) a first halosilane having the formula $RR^1SiX_2$, wherein X is F, Cl, Br, or I, and each R and $R^1$, independently, is X, H, or a lower alkyl group; and
   (b) a first primary amine compound having the formula $R^2NH_2$, wherein $R^2$ is H or a lower alkyl group to form a reaction product; and
   (c) reacting said reaction product with a second primary amine compound having the formula $R^3NH_2$, wherein $R^3$ is H or a lower alkyl group, $R^3$ being different from $R^2$, to form said organosilazane;
   heating said organosilazane in an inert atmosphere to form a polysilazane; and
   heating said polysilazane in an inert atmosphere to form said ceramic material.

2. The method of claim 1 wherein said polysilazane is heated at a temperature from about 250° C. to about 1200° C.

3. The method of claim 1 wherein there is reacted with said first halosilane, said first primary amine compound and said second primary amine compound a second halosilane different from said first halosilane and having the formula $R^4R^5R^6SiX$, wherein X is F, Cl, Br, or I, and each $R^4$, $R^5$, and $R^6$, independently, is X, H, or a lower alkyl group.

4. The method of claim 1 wherein said first halosilane is a trihalosilane.

5. The method of claim 4 wherein said trihalosilane has the formula $CH_3SiCl_3$.

6. The method of claim 1 wherein $R^2$ is H and $R^3$ is a lower alkyl group.

7. The method of claim 6 wherein $R^3$ is $CH_3$.

8. The method of claim 3 wherein said first halosilane is a trihalosilane, said second halosilane is a dihalosilane, and the mole ratio of said first halosilane to said second halosilane is about 2:1.

9. The method of claim 3 wherein said first halosilane is a dihalosilane, said second halosilane is a tetrahalosilane, and the mole ratio of said first halosilane to said second halosilane is about 2:1.

10. The method of claim 3 wherein said first halosilane has the formula $CH_3SiCl_3$ and said second halosilane has the formula $CH_3SiHCl_2$.

11. The method of claim 3 wherein said first halosilane has the formula $HSiCl_3$ and said second halosilane has the formula $H_2SiCl_2$.

12. The method of claim 3 wherein said first halosilane has the formula $CH_3SiHCl_2$ and said second halosilane has the formula $SiCl_4$.

13. The method of claim 3 wherein said first halosilane has the formula $H_2SiCl_2$ and said second halosilane has the formula $SiCl_4$.

14. The method of claim 3 wherein said first halosilane has the formula $HSiCl_3$ and said second halosilane has the formula $CH_3SiHCl_2$.

* * * * *

UNITED STATES PATENT AND TRADEMARK OFFICE
CERTIFICATE OF CORRECTION

PATENT NO. : 4,983,552
DATED : 1/8/91
INVENTOR(S) : Anthony A. Gallo

It is certified that error appears in the above-identified patent and that said Letters Patent is hereby corrected as shown below:

Column 1, under "Related U.S. Application Data", insert --4,778,907, 10/18/88--.

Column 1, line 28, delete the comma after "$R_2$".

Column 1, line 61, "P" in "Preferably" should be lowercase.

Column 2, line 62, "P" in "Participate" should be lowercase.

Column 3, line 31, --,$NH_3$,-- is missing between "$CH_3SiCl_3$" and "$CH_3NH_2$".

Column 3, line 57, "$CH_2NH_3$" should be --$CH_3NH_2$--.

Signed and Sealed this

Twenty-second Day of September, 1992

Attest:

DOUGLAS B. COMER

Attesting Officer    Acting Commissioner of Patents and Trademarks